United States Patent
Enomoto

(10) Patent No.: US 6,840,934 B2
(45) Date of Patent: Jan. 11, 2005

(54) LASER TREATMENT APPARATUS

(75) Inventor: Masanori Enomoto, Nishio (JP)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 10/202,848

(22) Filed: Jul. 26, 2002

(65) Prior Publication Data

US 2003/0028181 A1 Feb. 6, 2003

(30) Foreign Application Priority Data

Aug. 3, 2001 (JP) .................................... 2001-236000

(51) Int. Cl.$^7$ .............................................. A61B 18/20
(52) U.S. Cl. ........................................ 606/19; 606/13
(58) Field of Search ................... 606/13–19, 9, 606/10; 607/89

(56) References Cited

U.S. PATENT DOCUMENTS

| | | | |
|---|---|---|---|
| 3,913,582 A | * 10/1975 | Sharon ........................ | 606/10 |
| 4,270,845 A | 6/1981 | Takizawa et al. | |
| 4,497,319 A | * 2/1985 | Sekine et al. ................ | 606/10 |
| 4,532,400 A | * 7/1985 | Toida et al. .................. | 606/10 |
| 4,698,482 A | * 10/1987 | Monteith et al. ...... | 219/121.79 |
| 4,917,083 A | * 4/1990 | Harrington et al. ........... | 606/15 |
| 5,474,449 A | * 12/1995 | Loge et al. .................... | 606/19 |
| 5,738,681 A | * 4/1998 | Shimizu ....................... | 606/17 |
| 5,954,711 A | * 9/1999 | Ozaki et al. .................. | 606/10 |
| 6,117,129 A | 9/2000 | Mukai | |

FOREIGN PATENT DOCUMENTS

| | | |
|---|---|---|
| JP | 52-84890 | 7/1977 |
| JP | A 2001-95931 | 4/2001 |

* cited by examiner

Primary Examiner—Roy D. Gibson
Assistant Examiner—Henry M Johnson, III
(74) Attorney, Agent, or Firm—Oliff & Berridge, PLC

(57) ABSTRACT

A laser treatment apparatus for performing treatment by irradiating a part to be treated by a laser beam for treatment is disclosed. This apparatus includes a laser source which emits the treatment laser beam; a multi-articulated arm for delivering the treatment laser beam emitted from the laser source, the arm including a plurality of light delivery pipes at least one of which is axially extensible, a joint part for jointing the light delivery pipes, the joint part being rotatable with respect to at least one of the pipes jointed by the joint part, a reflection mirror disposed in the joint part; and a hand-piece connected to an end of the arm and used for irradiating the treatment laser beam delivered therein through the arm to the treatment part.

4 Claims, 4 Drawing Sheets

LASER TREATMENT APPARATUS

BACKGROUND OF THE INVENTION

1. Field of the Invention

The present invention relates to a laser treatment apparatus having a multi-articulated arm.

2. Description of Related Art

There have been known a laser treatment apparatus for performing treatment by irradiating a part to be treated by a laser beam for treatment. For instance, a laser treatment apparatus which emits a carbon dioxide laser beam having infrared wavelengths has been used for plastic treatment for removing wrinkles, birthmarks, etc. of patients.

In an apparatus of this type, the treatment beam emitted from a laser source is guided through a multi-articulated arm to a hand-piece mounted on an end of the arm and emerges therefrom to irradiate a treatment part. The arm is provided with a plurality of light delivery pipes and joints each jointing the pipes. In each joint, a reflection mirror is disposed. An operator manipulates the arm to position or put the hand-piece onto a target treatment part.

If treatment needs to be performed on a wide range, for instance, the arm may not be long enough to reach a target treatment part. In this case, the operator needs to move a main unit of the apparatus until the hand-piece can reach the treatment part. This work would be troublesome to the operator and cause a delay in treatment. If a fixed total length of the arm is made too long to solve the above problem, it would be hard to handle.

SUMMARY OF THE INVENTION

The present invention has been made in view of the above circumstances and has an object to overcome the above problems and to provide a laser treatment apparatus that is provided with a multi-articulated arm and capable of irradiating a treatment part of a wider range by a laser beam for treatment without the need for movement of the apparatus main unit every time treatment is performed.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a laser treatment apparatus for performing treatment by irradiating a treatment part with a laser beam for treatment, the apparatus including: a laser source which emits the treatment laser beam; a multi-articulated arm for delivering the treatment laser beam emitted from the laser source, the arm including: a plurality of light delivery pipes at least one of which is axially extensible, a joint part for jointing the light delivery pipes, the joint part being rotatable with respect to at least one of the pipes jointed by the joint part, a reflection mirror disposed in the joint part; and a hand-piece connected to an end of the arm and used for irradiating the treatment laser beam delivered therein through the arm to the treatment part.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
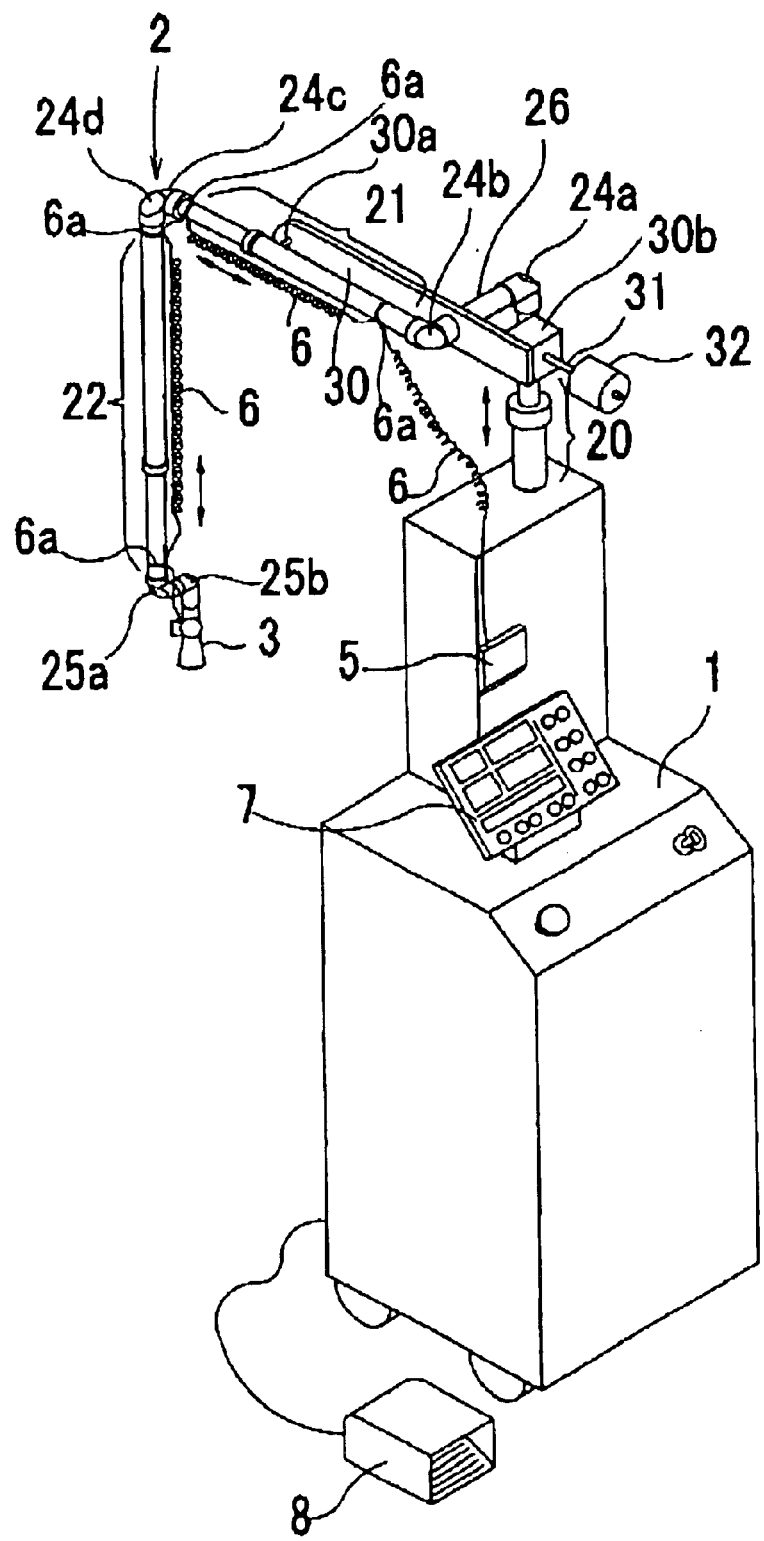
FIG. 1 is a schematic perspective view of a laser treatment apparatus in an embodiment according to the present invention.
Figure 2:
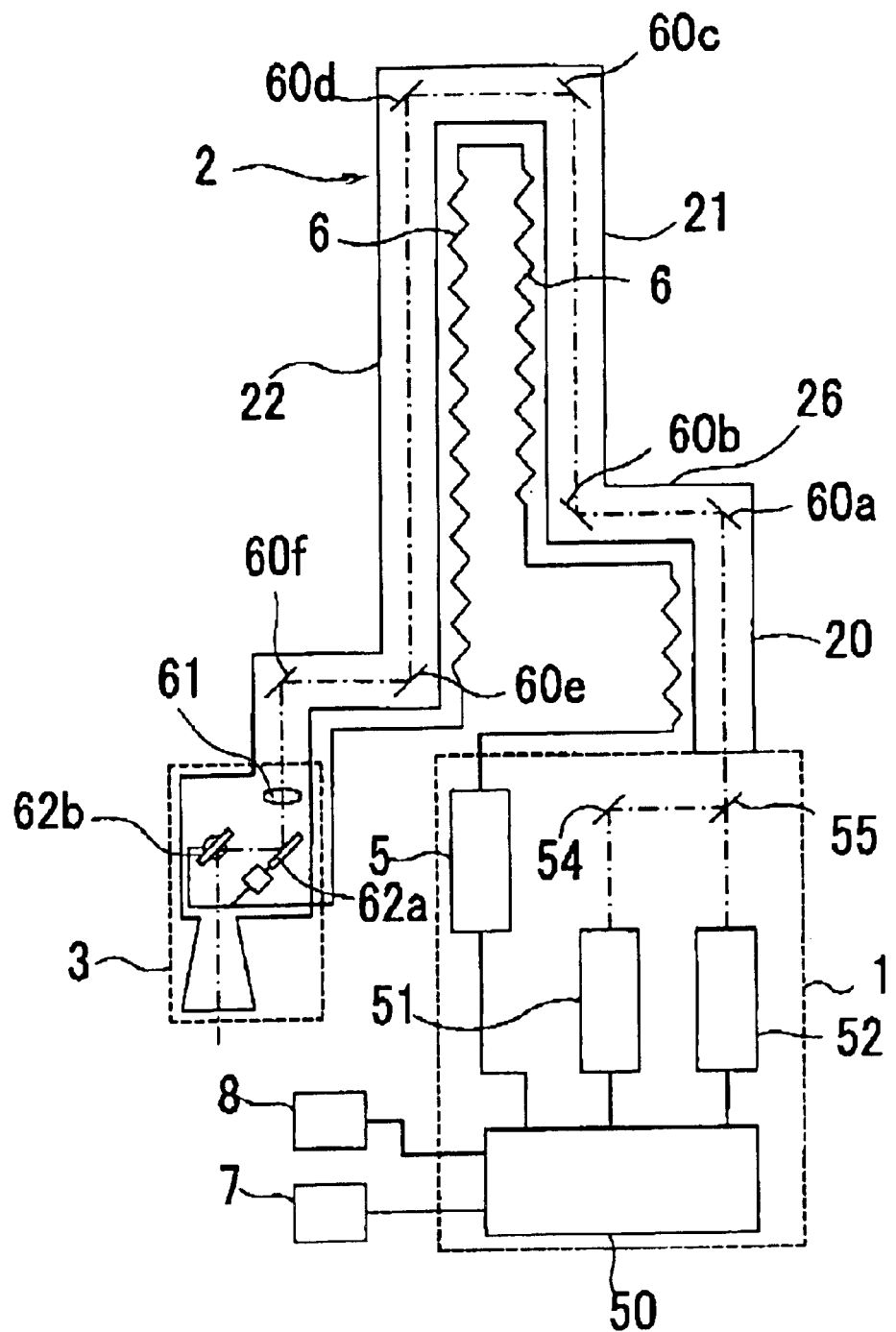
FIG. 2 is a schematic structural view of an optical system and a control system of the apparatus.

A detailed description of a preferred embodiment of a laser treatment apparatus embodying the present invention will now be given referring to the accompanying drawings. FIG. 1 is a schematic perspective view of the laser treatment apparatus for performing treatment to remove wrinkles and others of a skin. FIG. 2 is a schematic structural view of an optical system and a control system of the apparatus.

Numeral 1 is a main unit of the laser treatment apparatus. In this main unit 1, there are arranged a laser source 51 for treatment, a laser source 52 for aiming, a light delivery optical system, and a control part 50 for executing control of each part of the apparatus, and others. In the present embodiment, the laser source 51 is a $CO_2$ laser source which emits an infrared laser beam and the light source 52 is a laser diode which emits a red laser beam. The light delivery optical system is provided with a reflection mirror 54 which reflects the treatment beam emitted from the laser source 51 and a dichroic mirror 55 which brings the treatment beam and the aiming beam emitted from the laser source 52 into coaxial relation. The dichroic mirror 55 has a property of reflecting the treatment beam and allowing the aiming beam to pass therethrough. The laser source 51 and the laser source 52 both emit parallel laser beams.

Numeral 2 is a multi-articulated arm. Numeral 3 is a hand-piece unit for scanning, internally provided with driven mirrors 62a and 62b for causing each laser beam to scan a treatment part in X- and Y-directions. This hand-piece unit 3 is attached to an end of the arm 2 by joints 25a and 25b. Numeral 6 is a communication cable for sending signals from the control part 50 to drivingly control the mirrors 62a and 62b. Numeral 5 is a connector for connecting the cable 6 to the main unit 1 side. Numeral 7 is a control panel for input of various setting conditions such as a laser irradiation condition. Numeral 8 is a footswitch for generating a trigger signal to start laser irradiation.

Figure 4:
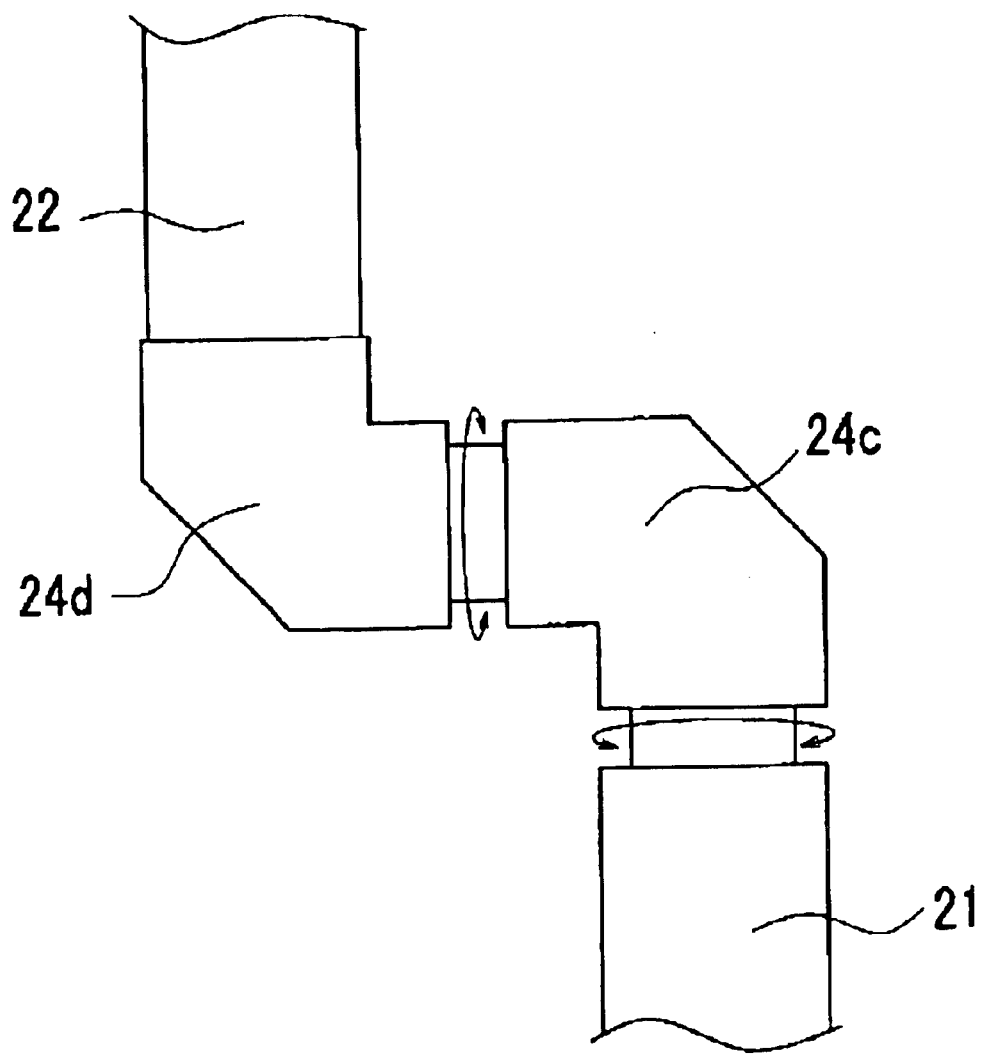
FIG. 4 is a schematic structural view of joints and peripheral parts thereof.

The arm 2 includes a columnar support 20 extending upward from the top of the main unit 1 and light delivery pipe assemblies 21 and 22 which are constructed to be extensible (telescopic) in respective axial directions (as indicated by arrows in FIG. 1). The extending structure will be mentioned later. The columnar support 20 and the light delivery pipe assembly 21 are jointed by joints 24a and 24b which have therein mirrors 60a and 60b respectively. The pipe assemblies 21 and 22 are similarly jointed by joints 24c and 24d which have therein mirrors 60c and 60d respectively. The joint 24a is rotatable with respect to the columnar support 20; the joint 24b is rotatable with respect to an intermediate pipe 26 mentioned later; the joint 24c is rotatable with respect to the light delivery pipe assembly 21; and the joint 24d is rotatable with respect to the joint 24c (see FIG. 4). It is to be noted that an intermediate pipe may additionally be provided between the joints 24c and 24d. In this case, the joint 24d is brought in rotatable relation to that intermediate pipe. The above configuration enables an operator to freely move the arm 2 by holding the hand-piece unit 3 by hand.

The intermediate pipe 26 is arranged between the joints 24a and 24b. To this pipe 26, a balance arm 30 is attached rotatably around the central axis of the intermediate pipe 26. An end of the balance arm 30 is connected to the light delivery pipe assembly 21 with a screw 30a. A balance weight 32 is rotatably attached on a rod 31 extending from a rear end part 30b of the balance arm 30. When rotated, the balance weight 32 moves in the axial direction of the rod 31. By adjustment of the position of the weight 32, the weight balance of the arm 2 can be controlled. An adjustable range of the weight balance by the weight 32 is the range in which the arm 2 can be kept in weight balance in both of the case where at least the light delivery pipe assemblies 21 and 22 are both extended to a maximum total length and the other case where the assemblies 21 and 22 are both contracted (retracted) to a minimum total length. This makes it possible to prevent the weight of the arm 2 from leaning to the hand-piece unit 3 side even when the total length of the arm 2 is changed, so that the hand-piece unit 3 can be prevented from bumping against a floor of an operating room, the main unit 1, and others. Furthermore, the operability of the arm 2 can be enhanced.

In the joints 25a and 25b, mirrors 60e and 60f are arranged respectively, which direct each laser beam delivered through the arm 2 (the light delivery pipe assemblies 21, 22, and others) to the hand-piece unit 3. These joints 25a and 25b enable free movement of the hand-piece unit 3 with respect to the arm 2. The hand-piece unit 3 is internally provided with a condensing lens 61 for converging each laser beam delivered into the unit 3 at a predetermined distance and galvano-mirrors used as the driven mirrors 62a and 62b.

The cable 6 is attached to the light delivery pipe assemblies 21 and 22 with plural belts 6a in order to prevent the cable 6 from interfering with treatment operation or work. The cable 6 takes the shape of a helical spring so as to be stretchable in the vicinity of the extensible portions of the arm 2 (i.e. the axially extensible portions of arm constituting components). Thus, the length of the cable 6 can be changed at any time in response to the total length of the arm 2 even when the arm 2 is extended or contracted (retracted). The cable 6 thus partially having a helical spring shape can be prevented from sagging and interfering with the treatment operation even when the total length of the arm 2 is contracted.

Figure 3:
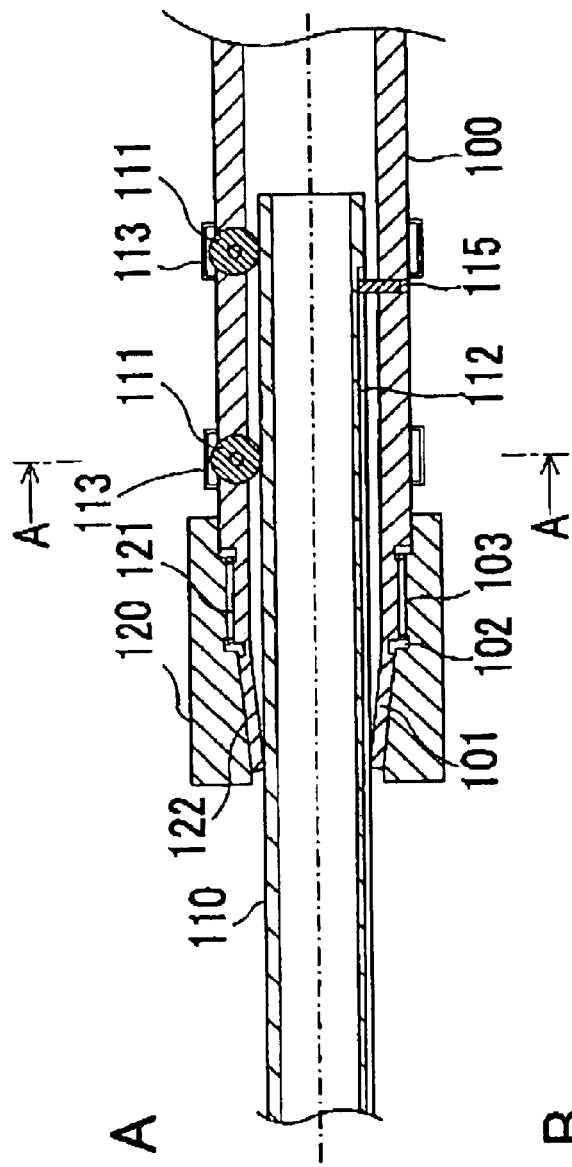
FIG. 3A is a longitudinal sectional view of an extending mechanism of a multi-articulated arm, corresponding to a sectional view taken along line B—B in FIG. 3B.
FIG. 3B is a cross sectional view of the extending mechanism, corresponding to a sectional view taken along line A—A in FIG. 3A.
Figure 3:
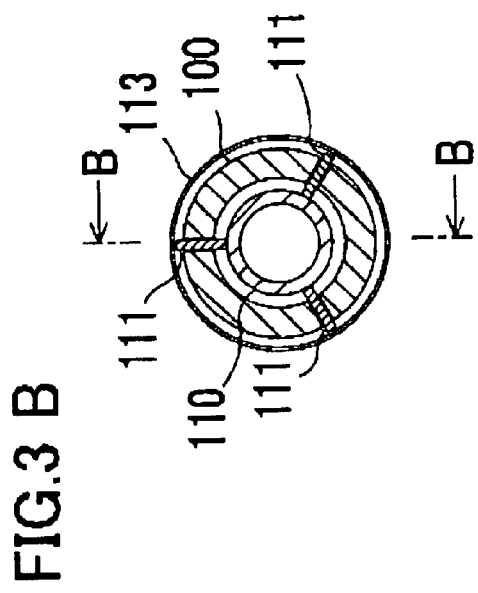

FIGS. 3A and 3B are schematic structural views of the extending mechanism of the light delivery pipe assembly 21; more specifically, FIG. 3A shows a longitudinal sectional view of the light delivery pipe assembly 21 along the axial direction thereof, which is a section taken along line B—B in FIG. 3B, and FIG. 3B shows a cross sectional view of the pipe assembly 21, which is a section taken along line A—A in FIG. 3A. The columnar support 20 and the other light delivery pipe assembly 22 are basically the same in structure and therefore the explanation thereof is omitted.

The light delivery pipe assembly 21 is constructed of two pipes of different diameters (an outer pipe 100 and an inner pipe 110) and a screw-operated locking member 120. The inner pipe 110 is placed to be axially slidable (movable) in the outer pipe 100. An end of the outer pipe 100 is formed with a tapered portion 101. A circumferential groove 102 is formed in a back portion of the tapered portion 101 over the entire outer periphery of the outer pipe 100 to reduce the thickness of the back portion. The tapered portion 101 is also formed with a plurality of unillustrated slits (cutouts) axially extending and being arranged in circumferentially spaced relation. With the groove 102 and the slits, the tapered portion 101 can be constricted in a direction toward the central axis (i.e. in an inward direction).

The screw-operated locking member 120 of a cylindrical shape is formed with a female screw 121 on an inner wall so that the female screw 121 engages with a male screw 103 formed on the back (the right in FIG. 3A) of the tapered portion 101 of the outer pipe 100. On the inner wall at the front (the left in FIG. 3A) of the female screw 121, the locking member 120 is formed with a tapered portion 122 having an inner diameter tapering down to an opposite side of the female screw 121. Accordingly, as the locking member 120 screwed on the outer pipe 100 is fastened, the tapered portion 122 diametrically constricts the tapered portion 101. When the locking member 120 is further fastened, the tapered portion 101 is correspondingly constricted, thereby fixedly holding the inner pipe 110 at an arbitrary position against sliding in the outer pipe 100.

The outer pipe 100 is provided with bearings 111 in groups of three each, one group being disposed close to an end portion of the outer pipe 100 and the other being disposed close to a center portion thereof so that the bearings 111 receive the inner pipe 110 movably in its axial direction. The three bearings 111 of each group are located at 120° intervals peripherally of the outer pipe 100 to support the inner pipe 110. These bearings 111 enable smooth movement of the inner pipe 110 while preventing the occurrence of rattling between the inner pipe 110 and the outer pipe 100. To minimize the occurrence of rattling, the two groups of bearings 111 arranged close to the end portion and the center portion respectively are preferably placed as apart from each other as possible.

In the present embodiment, furthermore, a straight pin having an eccentric axis is inserted in one of the three bearings 111. By rotation of the straight pin, the corresponding bearing 111 can be finely moved in the diametrical direction of the inner pipe 110. Thus, the three bearings 111 press against the inner pipe 110 to more effectively prevent the rattling during movement of the inner pipe 110. It is to be noted that numeral 113 is a bearing protection cover.

Numeral 115 is a stopper pin for preventing the inner pipe 110 from completely coming off from the outer pipe 100. This pin 115 is attached to the outer pipe 100 with a tip end engaged with a linear groove 112 formed on the outer wall of the inner pipe 110 along its axial direction to restrict the amount (length) of the inner pipe 110 to be pulled out of the outer pipe 100.

It is to be noted that an inner pipe 110 of the columnar support 20 is placed so as to be vertically movable in an outer pipe 100, and therefore the extending mechanism of the columnar support 20 preferably includes a mechanism for always upwardly urging the inner pipe 110 in the outer pipe 100. For instance, this mechanism may be constructed of a spring or a combination of a pulley and a weight.

In the laser treatment apparatus having the above structure, the extending operation of the multi-articulated arm 2 is explained below. The operator changes respective total lengths of the columnar support 20 and the light delivery pipe assemblies 21 and 22 to obtain a required length of the arm 2. To be more specifically, the operator appropriately loosens the locking members 120 of the columnar support 20 and the light delivery pipe assemblies 21 and 22 to pull out or retract the inner pipes 110 to obtain each required length. After reach inner pipe 110 is pulled out or retracted, the operator fastens each locking member 120 to completely lock that length. Each inner pipe 110 thus fixedly held by each locking member 120 will not cause misalignment of the optical axis due to the rattling. Even when the arm 2 is used while the locking members 120 are loosened, the bearings 111 attached to the inner pipe 110 can prevent the rattling.

After adjustment of the total length of the arm 2, the weight 32 is rotated to adjust the position thereof so that the hand-piece 3 can keep a balance without unnecessarily moving up and down even after the operator releases his hand from the arm 2. In addition of the use of the weight 32, the balance adjusting mechanism may include a spring in the intermediate pipe 26 so that the balance of the arm 2 can be maintained by control of the spring force of the spring.

In the present embodiment, each portion of the cable 6 arranged along each extensible portion of the arm 2 has a helical spring shape, but it is not necessarily limited thereto. For instance, in a position near the columnar support 20 or other places where the cable 6 will not interfere with the treatment operation, the cable 6 may have any shape other than a helical spring shape.

The multi-articulated arm in the present embodiment is constructed to be extensible or telescopic. Alternatively, plural multi-articulated arms (light delivery pipe assemblies) of different total lengths may be prepared to permit replacement thereof as needed.

According to the present invention, as explained above, the multi-articulated arm is configured to have changeable total length. This can eliminate the need to move the main unit in correspondence with the position of the treatment part.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. A laser treatment apparatus for performing treatment by irradiating a treatment part with a laser beam for treatment, the apparatus including:
   a laser source which emits the treatment laser beam;
   a multi-articulated arm for delivering the treatment laser beam emitted from the laser source, the multi-articulated arm including:
      first and second light delivery pipes;
      a joint part for jointing the first and second light delivery pipes, the joint part being rotatable with respect to at least one of the first and second light delivery pipes jointed by the joint part; and
      a reflection mirror disposed in the joint part;
   a hand-piece connected to an end of the multi-articulated arm and used for irradiating the treatment laser beam delivered therein through the multi-articulated arm to the treatment part; and
   a weight balance adjustment unit which adjusts weight balance of the multi-articulated arm,
   wherein the first light delivery pipe is arranged at a laser source side, the second light delivery pipe is arranged at a hand-piece side and includes plural axially extensible light delivery pipes, and each extensible light delivery pipe includes an outer pipe and an inner pipe.
   the weight balance adjustment unit includes a balance arm attached to the first and second light delivery pipes and being rotatable around the first light delivery pipe and a balance weight attached to the balance arm so that a distance of the balance weight from the first light delivery pipe is changeable, and
   the second light delivery pipe is rotatable around the first light delivery pipe with the balance arm.

2. The laser treatment apparatus according to claim 1, wherein each extensible light delivery pipe includes an outer pipe, an inner pipe which is placed in the outer pipe so that the inner pipe is movable in an axial direction of the outer pipe, and a bearing for supporting the inner pipe movably in the axial direction.

3. The laser treatment apparatus according to claim 1, wherein the weight balance adjustment unit is adjustable to keep the weight balance of the multi-articulated arm in both of a case where the multi-articulated arm is extended to a maximum length and a case where the multi-articulated arm is contracted to a minimum length.

4. The laser treatment apparatus according to claim 1, further including:
   a control part which controls drive of the hand-piece, the control part being disposed apart from the hand-piece; and
   a communication cable which connects the hand-piece and the control part for sending control signals from the control part to the hand-piece, the cable being stretchable to extend and contract in response to extension and contraction of the light delivery pipe.

* * * * *